United States Patent
Shin et al.

(10) Patent No.: US 11,684,265 B2
(45) Date of Patent: *Jun. 27, 2023

(54) DISEASE PREDICTION MODEL GENERATION APPARATUS, AND APPARATUS AND METHOD FOR PREDICTING DISEASE

(71) Applicant: SAMSUNG ELECTRONICS CO., LTD., Suwon-si (KR)

(72) Inventors: Eui Seok Shin, Yongin-si (KR); Yun S Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 126 days.

This patent is subject to a terminal disclaimer.

(21) Appl. No.: 17/464,214

(22) Filed: Sep. 1, 2021

(65) Prior Publication Data
US 2021/0393133 A1 Dec. 23, 2021

Related U.S. Application Data

(63) Continuation of application No. 15/955,353, filed on Apr. 17, 2018, now Pat. No. 11,134,847.

(30) Foreign Application Priority Data

Sep. 13, 2017 (KR) .................. 10-2017-0117141

(51) Int. Cl.
| | | |
|---|---|---|
| *A61B 5/00* | (2006.01) | |
| *G16H 50/30* | (2018.01) | |
| *G16H 50/50* | (2018.01) | |
| *G16H 50/20* | (2018.01) | |
| *G16H 40/63* | (2018.01) | |

(52) U.S. Cl.
CPC .......... *A61B 5/0071* (2013.01); *A61B 5/0064* (2013.01); *A61B 5/0075* (2013.01); *G16H 40/63* (2018.01); *G16H 50/20* (2018.01); *G16H 50/30* (2018.01); *G16H 50/50* (2018.01)

(58) Field of Classification Search
None
See application file for complete search history.

(56) References Cited

U.S. PATENT DOCUMENTS

| | | |
|---|---|---|
| 6,933,154 B2 | 8/2005 | Schomacker et al. |
| 7,139,598 B2 | 11/2006 | Hull et al. |
| | (Continued) | |

FOREIGN PATENT DOCUMENTS

| | | |
|---|---|---|
| DE | 10 2006 026 173 A1 | 12/2007 |
| WO | 2011/159148 A2 | 12/2011 |

OTHER PUBLICATIONS

Communication dated Dec. 11, 2018, issued by the European Patent Office in counterpart European Application No. 18175919.2.
H. L. Lutgers et al., "Skin autofluorescence provides additional information to the UK Prospective Diabetes Study(UKPDS) risk score for the estimation of cardiovascular prognosis in type 2 diabetes mellitus", Diabetologia, vol. 52, Springer, Mar. 10, 2009, pp. 789-797.

(Continued)

*Primary Examiner* — Yi-Shan Yang
(74) *Attorney, Agent, or Firm* — Sughrue Mion, PLLC

(57) ABSTRACT

A disease prediction apparatus may include: a spectrometer configured to obtain an optical spectrum of a subject; and a processor configured to predict autofluorescence of the subject based on the optical spectrum by applying the optical spectrum to an autofluorescence prediction model, and predict a risk of developing a cardiovascular disease based on the predicted autofluorescence.

20 Claims, 7 Drawing Sheets

(56) References Cited

U.S. PATENT DOCUMENTS

| | | | |
|---|---|---|---|
| 7,328,052 B2 | 2/2008 | Samsoondar et al. | |
| 2004/0077950 A1 | 4/2004 | Marshik-Geurts et al. | |
| 2005/0228295 A1 | 10/2005 | Tan | |
| 2007/0024946 A1 | 2/2007 | Panasyuk et al. | |
| 2007/0073118 A1 | 3/2007 | Ridder et al. | |
| 2008/0103396 A1 | 5/2008 | Johnson et al. | |
| 2008/0269616 A1 | 10/2008 | Bloom et al. | |
| 2012/0242858 A1 | 9/2012 | Prigent et al. | |
| 2012/0283530 A1* | 11/2012 | Maynard | A61B 5/0071 600/479 |
| 2013/0131488 A1 | 5/2013 | Zeng et al. | |
| 2013/0217984 A1* | 8/2013 | Graaff | A61B 5/0059 600/316 |
| 2014/0316292 A1 | 10/2014 | McRae et al. | |
| 2017/0127983 A1 | 5/2017 | Spegazzini et al. | |
| 2017/0135645 A1 | 5/2017 | Shin et al. | |

OTHER PUBLICATIONS

McIntyre et al., "Skin autofluorescence and the association with renal and cardiovascular risk factors in chronic kidney disease stage 3". Clin. J. Am. Soc. Nephrol. 6: 2356-2363, 2011. (Year: 2001).

Meerwaldt et al., "Skin autofluoresence is a strong predictor of cardiac mortality in diabetes". Diabetes Care, vol. 30, No. 1, pp. 107-112, 2007. (Year: 2007).

Lutgers et al., "Skin autofluorescence as a noninvasive marker of vascular damage in patients with type 2 diabetes". Diabetes Care 29: 2654-2659, 2006. (Year: 2006).

Gerrits et al., "Skin autofluorescence—a tool to identify type 2 diabetic patients at risk for developing microvascular complications" Diabetes Care 31: 517-521,2008. (Year: 2008).

* cited by examiner

DISEASE PREDICTION MODEL GENERATION APPARATUS, AND APPARATUS AND METHOD FOR PREDICTING DISEASE

CROSS-REFERENCE TO RELATED APPLICATION(S)

This is a continuation of U.S. application Ser. No. 15/955,353, filed Apr. 17, 2018, which claims priority from Korean Patent Application No. 10-2017-0117141, filed on Sep. 13, 2017, in the Korean Intellectual Property Office, the disclosure of which are incorporated herein by reference in their entireties.

BACKGROUND

1. Field

Apparatuses and methods consistent with exemplary embodiments relate to a disease prediction model generation apparatus for predicting a disease by using a near-infrared spectrum, and an apparatus and method for predicting a disease.

2. Description of the Related Art

With the aging of body tissues or under long-term exposure to high concentrations of glucose, proteins such as collagen in body tissues or blood vessels become glycated by non-enzymatic reactions. These glycated proteins are called Advanced Glycation End products (AGEs).

As the amount of AGEs in the body tissues increases, elasticity of the body tissues is reduced as a result of protein denaturation. That is, when the glucose concentration in the blood remains high for a long period of time, glycation of proteins in the blood vessels is accelerated, reducing elasticity of the walls of blood vessels with glycated proteins, and increasing vascular permeability, as well as oxidative stress and inflammatory factors in the blood vessels.

Such protein denaturation in the blood vessels may be a factor in increasing cardiovascular disease risk such as arteriosclerosis and high blood pressure. Further, the increase in glycated proteins in the blood vessels includes increased glycation of collagen proteins in tissues of the dermal layer. Once protein glycation occurs, autofluorescence increases, which emanates when infrared light is radiated, such that a degree of glycation of proteins may be estimated by measuring the autofluorescence emanating when infrared light is radiated, and cardiovascular disease risk may be predicted based on the estimation.

SUMMARY

According to an aspect of an exemplary embodiment, there is provided a disease prediction apparatus, including: a spectrometer configured to obtain an optical spectrum of a subject; and a processor configured to predict autofluorescence of the subject based on the optical spectrum by applying the optical spectrum to an autofluorescence prediction model, and predict a risk of developing a cardiovascular disease based on the predicted autofluorescence.

The processor may be further configured to predict the risk of developing the cardiovascular disease based on the predicted autofluorescence and user information of the subject.

The user information may include at least one of age, gender, race, occupation, stature, body mass index (BMI), smoking status, hemoglobin A1c (HbA1c) concentration of the subject.

The autofluorescence prediction model may be a prediction model generated based on a correlation between a light absorbance of a test object at a wavelength of a light and an autofluorescence intensity of the test object in response to the light being incident onto the test object.

The processor may be further configured to predict the risk of developing the cardiovascular disease by applying the optical spectrum to a cardiovascular disease risk prediction model.

The cardiovascular disease risk prediction model may be a prediction model generated based on an optical spectrum of a test object and cardiovascular disease risk classification data which is pre-generated based on user information and autofluorescence of the test object.

The processor may be further configured to classify the risk of developing the cardiovascular disease by applying the user information and the autofluorescence of the subject to the cardiovascular disease risk prediction model.

The processor may be further configured to split the optical spectrum of the test object into one or more principal components, and predict the risk of developing the cardiovascular disease based on the principal components by using the cardiovascular disease risk prediction model.

The processor may be further configured to perform preprocessing on the obtained optical spectrum by using at least one preprocessing algorithm among Multiplicative Scattering Correction (MSC), Savitzky-Golay filter, and Standard Normal Variate (SNV) analysis.

The apparatus may further include an output interface configured to output at least one of a disease prediction result and warning information by using at least one of an acoustic method, a visual method, and a tactile method.

According to an aspect of another exemplary embodiment, there is provided a disease prediction model generation apparatus, including: a spectrometer configured to obtain an optical spectrum from a light that is emitted to and returned from a subject; and a processor configured to generate an autofluorescence prediction model based on a correlation between the optical spectrum and autofluorescence of the subject.

The apparatus may further include an autofluorescence obtainer configured to obtain autofluorescence measured by radiating a ultraviolet A light to a skin of the subject.

The processor may be further configured to generate the autofluorescence prediction model based on a light absorbance of the subject at a wavelength of the optical spectrum and the autofluorescence of the subject by using a partial least square (PLS) regression algorithm.

The processor may be further configured to generate a cardiovascular disease risk prediction model based on the optical spectrum of the subject and pre-generated cardiovascular disease risk classification data.

The cardiovascular disease risk prediction model may be generated into one or more groups according to at least one criterion of health information, and user information including a user's age, gender, race, occupation, stature, body mass index (BMI), smoking status, hemoglobin A1c (HbA1c) concentration.

According to an aspect of another exemplary embodiment, there is provided a disease prediction method, the method including: obtaining an optical spectrum of a subject; predicting autofluorescence of the subject by applying the optical spectrum to an autofluorescence prediction model generated based on a correlation between a light absorbance of a test object at a wavelength and an autofluorescence intensity of the test object; and predicting a risk of developing a cardiovascular disease of the subject based on the predicted autofluorescence.

The predicting the risk of developing the cardiovascular disease may include predicting the risk of developing the cardiovascular disease by applying the optical spectrum of the subject to a cardiovascular disease risk prediction model generated based on cardiovascular disease risk classification data.

The predicting the risk of developing the cardiovascular disease may include predicting the risk of developing the cardiovascular disease based on the predicted autofluorescence and user information of the subject.

The predicting the risk of developing the cardiovascular disease may include: dividing the optical spectrum of the subject into one or more principal components; and predicting the risk of developing the cardiovascular disease based on the principal components by using the cardiovascular disease risk prediction model.

The disease prediction method may further include outputting at least one of a disease prediction result and warning information by using at least one of a visual method, an acoustic method, and a tactile method.

BRIEF DESCRIPTION OF THE DRAWINGS

The above and/or other aspects will be more apparent by describing certain exemplary embodiments, with reference to the accompanying drawings, in which.

Figure 1:
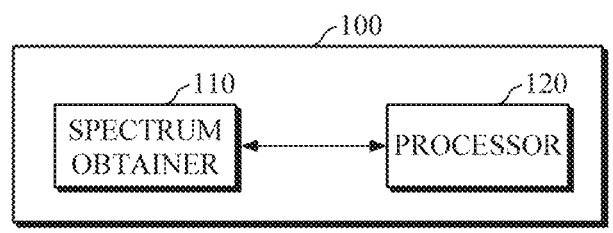
FIG. 1 is a block diagram illustrating a disease prediction apparatus according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list.

FIG. 1 is a block diagram illustrating a disease prediction apparatus according to an exemplary embodiment. The disease prediction apparatus 100 may obtain a skin spectrum, and may predict a disease by using a disease prediction model which is pre-generated for disease prediction.

For example, the disease prediction apparatus 100 may obtain a skin spectrum by emitting light onto a user's skin and detecting light which is reflected or scattered therefrom, and may analyze the absorbance or light intensity of the obtained skin spectrum in a specific wavelength range. In particular, the disease prediction apparatus 100 may store a prediction model which is pre-generated for disease prediction, and may predict at least one of autofluorescence and/or cardiovascular disease risk based on, for example, an autofluorescence prediction model and/or a cardiovascular disease risk prediction model.

The cardiovascular disease is a disease affecting the heart and main arteries, and examples thereof may include high blood pressure, ischemic heart disease, coronary artery disease, angina, myocardial infarction, arteriosclerosis, arrhythmia, cerebrovascular disease, stroke, and the like.

The disease prediction apparatus 100 may be implemented as a software module or may be manufactured in the form of a hardware chip to be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like. However, the electronic apparatus is not limited to these examples, and examples thereof may include various devices.

Referring to FIG. 1, the disease prediction apparatus 100 includes a spectrum obtainer 110 and a processor 120. Here, the processor 120 may include one or more processors, a memory, and a combination thereof.

The spectrum obtainer 110 may obtain a user's skin spectrum.

In the exemplary embodiment, the skin spectrum may refer to a skin near-infrared absorption spectrum or an optical absorption spectrum of a subject, which is measured from a light that is emitted to and then returned from a skin of the subject. However, the skin spectrum is not limited thereto, and may be a skin near-infrared transmission spectrum or a skin near-infrared reflectance spectrum.

The spectrum obtainer 110 may include a light source which emits light onto the subject, and a light detector which detects light reflected or scattered from the subject. The spectrum obtainer 110 may directly generate skin spectrum data by using the light detected by the light detector. The spectrum obtainer 110 may be referred to as a spectrometer.

Further, the spectrum obtainer 110 may communicate with an external device to receive skin spectrum data of a user from the external device. For example, the spectrum obtainer 110 may receive the skin spectrum data of the user from the external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra Wideband (UWB) communication, Ant+ communication, WIFI communication, Radio Frequency Identification (RFID) communication, and the like. However, this is merely exemplary and the communication is not limited thereto.

Further, examples of the external device may include a cellular phone, a smartphone, a tablet PC, a laptop computer, a personal digital assistant (PDA), a portable multimedia player (PMP), a navigation, an MP3 player, a digital camera, a wearable device, and the like. However, the external device is not limited thereto, and examples thereof may include various devices that may store skin spectrum data of a user.

The processor 120 may predict autofluorescence and/or cardiovascular disease risk based on a disease prediction model which is pre-generated for disease prediction.

In the exemplary embodiment, the processor 120 may predict autofluorescence for the skin spectrum by applying the obtained skin spectrum to an autofluorescence prediction model.

Here, the autofluorescence prediction model may be a prediction model which is pre-generated based on a correlation between absorbance at a wavelength of the skin spectrum and autofluorescence.

For example, the autofluorescence prediction model may be a prediction model which is pre-generated by using at least one skin spectrum, obtained from at least one test subject, as an independent variable, by radiating a ultraviolet A (UV-A) light in a wavelength range of 320 nm to 380 nm to the subject, and by using, as a dependent variable, a measured value of autofluorescence emanating from the skin after a UV-A light is radiated thereto. For example, the autofluorescence prediction model may be a prediction model generated by analyzing a correlation between the skin spectrum, obtained from the subject, and autofluorescence by using a partial least square (PLS) regression algorithm.

Further, the autofluorescence prediction model may be generated into one or more groups according to at least one criterion among a user's age, gender, race, occupation, stature, body mass index (BMI), smoking status, hemoglobin A1c (HbA1c) concentration in the blood, and health information.

Among the autofluorescence prediction models that are classified into one or more groups according to one criterion, the processor 120 may select an autofluorescence prediction model based on user information. For example, once a user's age, gender, and stature are input as the user information, the processor 120 may select an autofluorescence prediction model that is appropriate for the input user information.

For example, upon obtaining the skin spectrum, the processor 120 predicts autofluorescence, corresponding to the obtained skin spectrum, based on the autofluorescence prediction model. In this manner, the processor 120 may predict a user's autofluorescence without directly radiating ultraviolet rays to the skin.

In particular, by using at least one preprocessing algorithm among Multiplicative Scattering Correction (MSC), Savitzky-Golay filter, and Standard Normal Variate (SNV) analysis, the processor 120 may perform preprocessing on the obtained skin spectrum, and may predict autofluorescence for the skin spectrum by applying the preprocessed skin spectrum to the autofluorescence prediction model.

The processor 120 may predict a risk of developing a cardiovascular disease (i.e., a cardiovascular disease risk) based on the predicted autofluorescence.

For example, the processor 120 may predict the cardiovascular disease risk by predicting autofluorescence from the skin spectrum and by estimating a degree of protein glycation based on the predicted autofluorescence. In this case, the degree of protein glycation for autofluorescence is a degree of protein glycation for autofluorescence which is actually measured by radiating a UV-A light having a wavelength of 320 nm to 380 nm to the skin of a plurality of subjects, and may be data measured and collected in advance.

For example, the processor 120 may predict the cardiovascular disease risk by determining whether the predicted autofluorescence exceeds a predetermined threshold, or whether the predicted autofluorescence exceeds an average autofluorescence for a user's age, and may classify the cardiovascular disease risk into one or more categories according to a degree of excess.

In the embodiment, the processor 120 may predict the cardiovascular disease risk based on the predicted autofluorescence and the user information.

Here, the user information may include at least one of the following: a user's age, gender, race, occupation, stature, BMI, smoking status, HbA1c concentration in the blood, and health information. However, the user information is not limited thereto, and may include various types of personal information required for prediction of the cardiovascular disease risk.

For example, the processor 120 may predict autofluorescence based on the autofluorescence prediction model, and may predict the cardiovascular disease risk based on the predicted autofluorescence and a user's age.

For example, since glycation occurs by non-enzymatic reaction of proteins with the aging of human body tissues, and autofluorescence of the body tissues increases accordingly, the processor 120 may predict the cardiovascular disease risk by predicting autofluorescence and comparing the predicted autofluorescence with a reference autofluorescence for a user's age.

Further, the processor 120 may classify levels of the cardiovascular disease risk according to an extent in which the predicted autofluorescence exceeds the reference autofluorescence for a user's age. Here, the reference autofluorescence may be an average autofluorescence for a user's age, and may be set individually based on the user information.

In this manner, the disease prediction apparatus 100 may predict autofluorescence from the skin spectrum, and may predict the cardiovascular disease risk based on the predicted autofluorescence, thereby preventing a user's skin from being exposed to harmful ultraviolet rays.

In another example, the processor 120 may predict the cardiovascular disease risk by applying the skin spectrum to a cardiovascular disease risk prediction model, and may classify the cardiovascular disease risk.

Here, the cardiovascular disease risk prediction model may be a prediction model generated based on the skin spectrum and pre-generated cardiovascular disease risk classification data.

The cardiovascular disease risk classification data may include user information and risk assessment data based on autofluorescence for the user information. For example, the cardiovascular disease risk classification data may include cardiovascular disease risk that is estimated based on a user's age and skin fluorescence.

For example, the cardiovascular disease risk prediction model may be a prediction model generated based on a correlation between the skin spectrum, obtained from a subject, and the cardiovascular disease risk estimated based on the age and skin fluorescence of the subject.

For example, the cardiovascular disease risk prediction model may be a prediction model generated by using the skin spectrum, obtained from the subject, as an independent variable, by using, as a dependent variable, the cardiovascular disease risk estimated based on the autofluorescence and age of the subject, and by using Support vector machine (SVM) and Linear discriminant analysis. However, the cardiovascular disease risk prediction model is not limited thereto, and may use various regression analysis algorithms and machine learning for analyzing a correlation between the skin spectrum, obtained from the subject, and the cardiovascular disease risk estimated based on the autofluorescence and age of the subject.

Further, the cardiovascular disease risk prediction model may be generated into one or more groups according to at least one of the following: a user's age, gender, race, occupation, stature, BMI, smoking status, HbA1c concentration in the blood, and health information. In this case, among cardiovascular disease risk prediction models generated into one or more groups according to one or more criteria, the processor 120 may predict a disease by selecting an appropriate cardiovascular disease risk prediction model based on user information.

Upon obtaining a skin spectrum, the processor 120 applies the obtained skin spectrum to the cardiovascular disease risk prediction model, and compares the skin spectrum with risk assessment data which is based on autofluorescence, to determine the cardiovascular disease risk of a user by determining whether autofluorescence corresponding to the obtained skin spectrum exceeds an average autofluorescence for a user's age. The processor 120 may classify levels of the risk.

Figure 2:
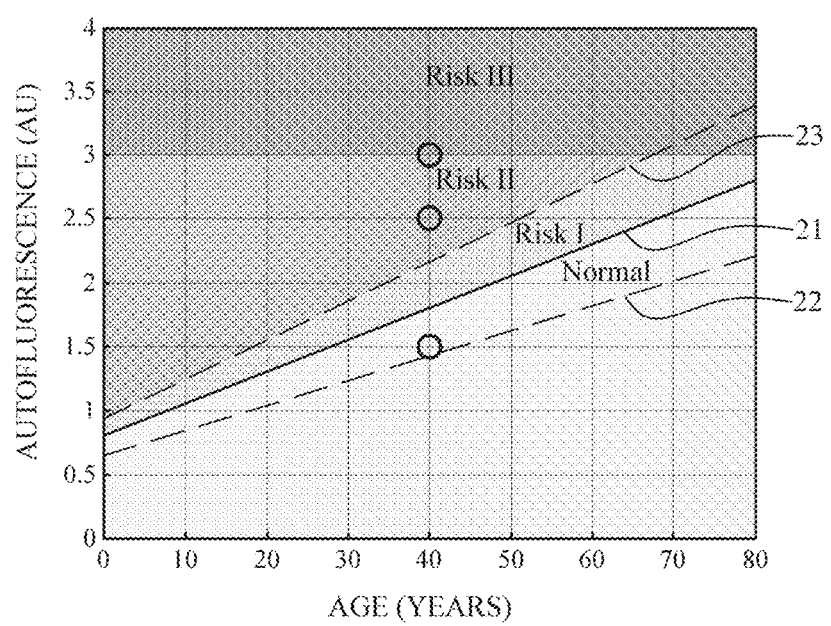
FIG. 2 is a graph indicating classification of cardiovascular disease risks according to an exemplary embodiment.

FIG. 2 is graphs indicating classification of cardiovascular disease risks. Referring to FIG. 2, reference numeral 21 indicates a graph using age as an independent variable, and using an average autofluorescence for the age as a dependent variable; reference numeral 22 indicates a graph using age as an independent variable, and subtracting standard deviation 1 from the average autofluorescence for the age; and reference numeral 23 is a graph using age as an independent variable and adding standard deviation 1 to the average autofluorescence for the age. The graphs 21-23 may be stored in a storage (e.g., a storage part 340 in FIG. 3) and the processor 120 may retrieve the graphs 21-23 from the storage to perform a cardiovascular disease risk prediction.

Referring to FIGS. 1 and 2, the processor 120 may predict cardiovascular disease risk of a user by applying a skin spectrum to a cardiovascular disease risk prediction model, and may classify the predicted cardiovascular disease risk.

For example, the processor 120 may classify cardiovascular disease risk of a user based on autofluorescence predicted according to the user's age.

For example, in the case where autofluorescence of a user, whose age is 40 years old, is 1.5 absorption unit (AU), cardiovascular disease risk of the user may be classified as normal because the combination of age 40 and 1.5 AU belongs to an area below the graph 21, which is labeled as "Normal". In the case where the autofluorescence is 2.5 AU, cardiovascular disease risk of the user may be classified as Risk II because the combination of age 40 and 2.5 AU belongs to an area above the graph 23, which is labeled as "Risk II". In the case where the autofluorescence exceeds 3 AU, cardiovascular disease risk of the user may be classified as Risk III, regardless of the age of the user.

In another example, upon obtaining a skin spectrum of the user, the processor 120 splits the obtained skin spectrum into one or more components, and may predict cardiovascular disease risk based on the components by using a cardiovascular disease risk prediction model. For example, the processor 120 may split the skin spectrum of the user into one or more principal components by using Principal Component Analysis (PCA), and may predict the cardiovascular disease risk based on the principal components by using the cardiovascular disease risk prediction model. Principal components may refer to a set of values of linearly uncorrelated variables.

For example, upon dividing the skin spectrum of the user into one or more principal components by using Principal Component Analysis (PCA), the processor 120 may predict the cardiovascular disease risk by using Support vector machine (SVM) or Linear discriminant analysis. However, the processor 120 is not limited thereto, and may predict the cardiovascular disease risk based on the skin spectrum of the user by using various regression analysis algorithms and machine learning.

Figure 3:
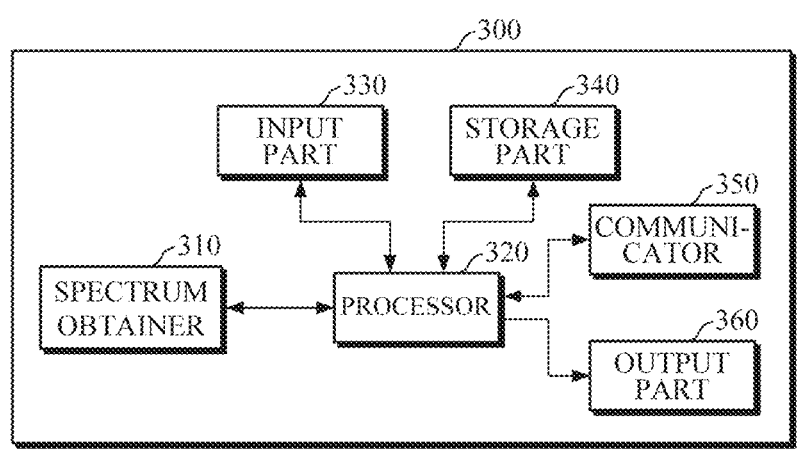
FIG. 3 is a block diagram illustrating a disease prediction apparatus according to another exemplary embodiment.

FIG. 3 is a block diagram illustrating another example of a disease prediction apparatus.

Referring to FIG. 3, the disease prediction apparatus 300 includes a spectrum obtainer 310, a processor 320, an input part (e.g., an input interface) 330, a storage part (e.g., a memory) 340, a communicator (e.g., a communication interface) 350, and an output part (e.g., an output interface) 360. Here, the spectrum obtainer 310 and the processor 320 may perform substantially the same operations as those of the spectrum obtainer 110 and the processor 120 described above with reference to FIG. 1, such that description below will be made based on details that do not overlap.

The input part 330 may receive input of various operation signals and data required for disease prediction from a user. In the embodiment, the input part 330 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

For example, the input part 330 may receive input of user information including at least one or more of age, gender, race, occupation, stature, BMI, smoking status, HbA1c concentration in the blood, and health information.

For example, based on the input information (e.g.: user information, etc.), the processor 320 may select an autofluorescence prediction model and/or a cardiovascular disease risk prediction model, which are classified and generated into one or more groups.

The storage part 340 may store programs or commands for operation of the disease prediction apparatus 300, and may store data input to and output from the disease prediction apparatus 300. For example, the storage part 340 may store user information input through the input part 330, data of the skin spectrum obtained by the spectrum obtainer 310, the autofluorescence prediction model and/or the cardiovascular disease risk prediction model, cardiovascular disease risk classification data, and the like.

The storage part 340 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the disease prediction apparatus 300 may operate an external storage medium, such as web storage and the like, which performs a storage function of the storage part 340 on the Internet.

The communicator 350 may perform communication with an external device. For example, the communicator 350 may transmit, to the external device, the user information input through the input part 330, the data of the skin spectrum obtained by the spectrum obtainer 310, a disease prediction result by the processor 320, and the like; or may receive various data, such as the user information, the skin spectrum, the autofluorescence prediction model, the cardiovascular disease risk prediction model, the cardiovascular disease risk classification data, and the like.

In this case, the external device may be medical equipment using a disease prediction model database (DB) and/or the disease prediction result, a printer to print out results, or a display to display the disease prediction result. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 350 may communicate with external devices by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra Wideband (UWB) communication, Ant+ communication, WIFI communication, Radio Frequency Identification (RFID) communication, 3G communication, 4G communication, 5G communication, and the like. However, this is merely exemplary and the communication is not limited thereto.

The output part 360 may output at least one or more of the disease prediction result and warning information by control of the processor 320.

For example, the output part 360 may output at least one or more of the disease prediction result and warning information by using at least one of an acoustic method, a visual method, and a tactile method. To this end, the output part 360 may include a display, a speaker, a vibrator, and the like.

Figure 4:
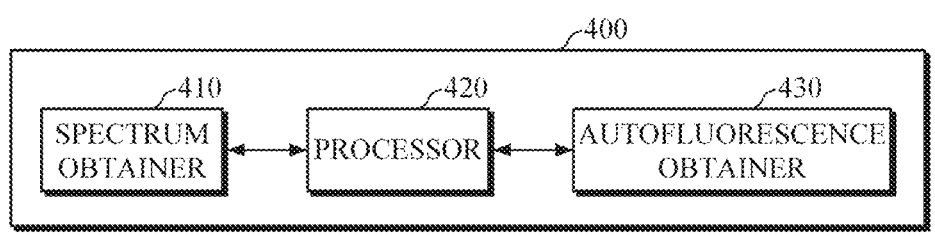
FIG. 4 is a block diagram illustrating a disease prediction model generation apparatus according to an exemplary embodiment.

FIG. 4 is a block diagram illustrating a disease prediction model generation apparatus according to an exemplary embodiment.

Referring to FIG. 4, the disease prediction model generation apparatus 400 includes a spectrum obtainer 410 and a processor 420. Here, the processor 420 may include one or more processors, a memory, and a combination thereof.

The spectrum obtainer 410 may obtain a skin spectrum of a subject.

In the exemplary embodiment, the skin spectrum may be a skin near-infrared absorption spectrum which is measured by emitting near-infrared rays onto the skin of the subject.

In this case, the spectrum obtainer 410 may include a light source which emits light onto the subject, and a light detector which detects light reflected or scattered from the subject. The spectrum obtainer 410 may directly generate skin spectrum data by using the light detected by the light detector, or may receive skin spectrum data of the subject from an external device by communicating with the external device.

The processor 420 may generate an autofluorescence prediction model based on a correlation between the skin spectrum and autofluorescence of the subject.

In the embodiment, the processor 420 may generate the autofluorescence prediction model based on a correlation between absorbance of a skin near-infrared spectrum, obtained from spectrum data of light detected after near-infrared light is emitted onto the skin of the subject, and autofluorescence measured for the skin of the subject.

For example, the disease prediction model generation apparatus 400 may further include an autofluorescence obtainer which obtains autofluorescence by radiating a UV-A light having a wavelength of 320 nm to 380 nm to the skin of the subject, and the processor 420 may generate the autofluorescence prediction model based on the absorbance of the skin spectrum, obtained from the subject, and autofluorescence of the subject. The autofluorescence obtainer may include a light emitter that radiates a UV-A light, and a light detector that detects an intensity of autofluorescence that is emitted from the subject in response to the UV-A light being incident onto the subject.

For example, the processor 420 may obtain the skin spectrum from the subject and may generate the autofluorescence prediction model by using, as an independent variable, a result of preprocessing of the obtained skin spectrum performed by using at least one preprocessing filter among Multiplicative Scattering Correction (MSC), Standard Normal Variate (SNV) analysis, and/or Savitzky-Golay filter, by using, as a dependent variable, autofluorescence obtained by radiating a UV-A light having a wavelength of 320 nm to 380 nm to the skin of the subject and by using a partial least square (PLS) regression algorithm.

In another example, the processor 420 may generate a cardiovascular disease risk prediction model based on the skin spectrum of the subject and the pre-generated cardiovascular disease risk classification data. For example, the processor 420 may generate the cardiovascular disease risk prediction model based on the cardiovascular disease risk classification data, which includes user information and autofluorescence of the subject corresponding to the user information, and the skin spectrum of the subject.

In this case, the cardiovascular disease risk classification data may include the user information and risk assessment data based on autofluorescence for the user information. For example, the cardiovascular disease risk classification data may include cardiovascular disease risk estimated based on the age and skin fluorescence of the subject.

For example, the processor 420 may generate the cardiovascular disease risk prediction model based on a correlation between the skin spectrum, obtained from a subject, and the cardiovascular disease risk estimated based on the age and skin fluorescence of the subject For example, the processor 420 may generate the cardiovascular disease risk prediction model by using the skin spectrum, obtained from the subject, as an independent variable, by using, as a dependent variable, the cardiovascular disease risk estimated based on the autofluorescence and age of the subject, and by using Support vector machine (SVM) and Linear discriminant analysis. However, the processor 420 is not limited thereto, and may use various regression analysis algorithms and machine learning for analyzing a correlation between the skin spectrum obtained from the subject and the cardiovascular disease risk estimated based on the autofluorescence and age of the subject.

Further, the processor 420 may generate the cardiovascular disease risk prediction model into one or more groups according to at least one criterion among a user's age, gender, race, occupation, stature, BMI, smoking status, HbA1c concentration in the blood, and health information.

Figure 5:
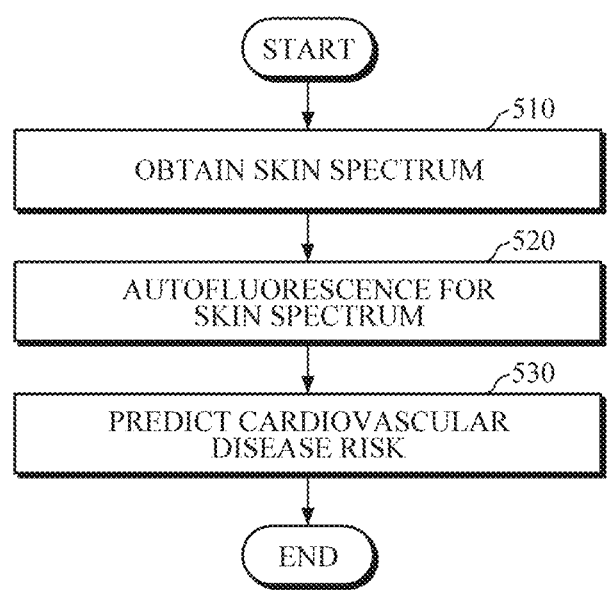
FIG. 5 is a flowchart illustrating a disease prediction method according to an exemplary embodiment.

FIG. 5 is a flowchart illustrating a disease prediction method according to an exemplary embodiment. The disease prediction method of FIG. 5 may be performed by the disease prediction apparatuses 100 and 200 of FIGS. 1 and 2.

Referring to FIGS. 1 and 5, the disease prediction apparatus 100 may obtain a user's skin spectrum in operation 510.

In the exemplary embodiment, the skin spectrum may refer to a skin near-infrared absorption spectrum or an optical absorption spectrum of a subject, which is measured from a light that is emitted to and then returned from a skin of the subject. However, the skin spectrum is not limited thereto, and may be a skin near-infrared transmission spectrum or a skin near-infrared reflectance spectrum.

For example, the disease prediction apparatus 100 may directly generate skin spectrum data by emitting light onto a subject and detecting light reflected or scattered therefrom. However, the disease prediction apparatus 100 is not limited thereto, and may receive skin spectrum data of the user from an external device by communicating with the external device.

The disease prediction apparatus 100 may predict autofluorescence for the skin spectrum by applying the obtained skin spectrum to an autofluorescence prediction model in operation 520.

In the exemplary embodiment, the disease prediction apparatus 100 may predict the autofluorescence for the skin spectrum by applying the obtained skin spectrum to the autofluorescence prediction model which is pre-generated based on a correlation between absorbance at a wavelength of the skin spectrum and autofluorescence.

In this case, the autofluorescence prediction model may be a prediction model which is pre-generated by using the skin spectrum, obtained from a subject, as an independent variable, by radiating a UV-A light in a wavelength range of 320 nm to 380 nm to the subject, and by using, as a dependent variable, a measured value of autofluorescence emanating from the skin after the UV-A light is radiated thereto. For example, the autofluorescence prediction model may be a prediction model generated by analyzing a correlation between the skin spectrum, obtained from the subject, and autofluorescence by using a partial least square (PLS) regression algorithm.

Upon obtaining the skin spectrum, the disease prediction apparatus 100 may predict autofluorescence, corresponding to the obtained skin spectrum, based on the autofluorescence prediction model. In this manner, the disease prediction apparatus 100 may predict a user's autofluorescence without directly radiating ultraviolet rays to the skin.

In this case, by using at least one preprocessing algorithm among Multiplicative Scattering Correction (MSC), Savitzky-Golay filter, and Standard Normal Variate (SNV) analysis, the disease prediction apparatus 100 may perform preprocessing of the obtained skin spectrum, and may predict autofluorescence for the skin spectrum by applying the preprocessed skin spectrum to the autofluorescence prediction model.

Upon predicting the autofluorescence, the disease prediction apparatus 100 may predict cardiovascular disease risk in operation 530. For example, the disease prediction apparatus 100 may estimate a degree of protein glycation based on the predicted autofluorescence, and may predict the cardiovascular disease risk based on the estimated degree of protein glycation.

For example, the disease prediction apparatus 100 may predict the cardiovascular disease risk by determining whether the predicted autofluorescence exceeds a predetermined threshold, or whether the predicted autofluorescence exceeds an average autofluorescence for a user's age, and may classify the cardiovascular disease risk into one or more categories according to a degree of excess.

In the exemplary embodiment, the disease prediction apparatus 100 may predict the cardiovascular disease risk based on the predicted autofluorescence, and the user information including at least one of the following: a user's age, gender, race, occupation, stature, BMI, smoking status, HbA1c concentration in the blood, and health information.

For example, since glycation occurs by non-enzymatic reaction of proteins with the aging of human body tissues, and autofluorescence of the body tissues increases accordingly, the disease prediction apparatus 100 may predict the cardiovascular disease risk by predicting autofluorescence and comparing the predicted autofluorescence with a reference autofluorescence for a user's age.

Figure 6:
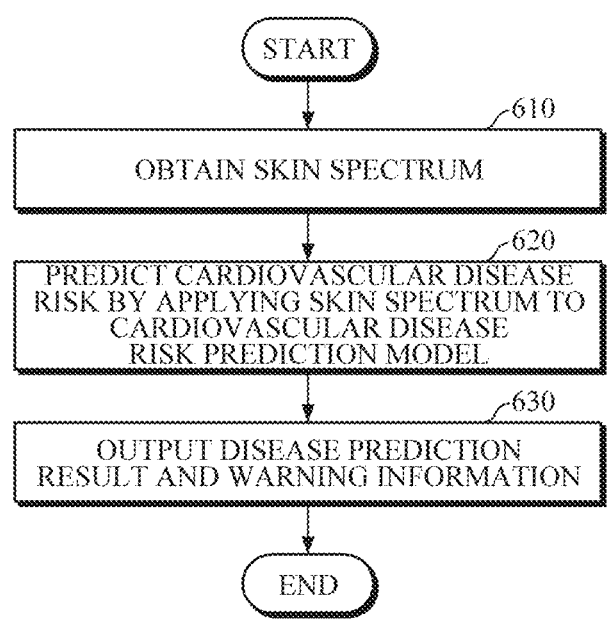
FIG. 6 is a flowchart illustrating a disease prediction method according to an exemplary embodiment.

FIG. 6 is a flowchart illustrating a disease prediction method according to another exemplary embodiment. The disease prediction method of FIG. 6 may be performed by the disease prediction apparatuses 100 and 200 of FIGS. 1 and 2.

Referring to FIGS. 2 and 6, the disease prediction apparatus 200 may obtain a user's skin spectrum in operation 610.

For example, the disease prediction apparatus 200 may directly generate skin spectrum data by emitting light onto a subject and detecting light reflected or scattered therefrom. However, the disease prediction apparatus 200 is not limited thereto, and may receive skin spectrum data of the user from an external device by communicating with the external device.

Upon obtaining the skin spectrum, the disease prediction apparatus 200 may predict cardiovascular disease risk by applying the skin spectrum to a cardiovascular disease risk prediction model, and may classify the cardiovascular disease risk in operation 620.

In the exemplary embodiment, the disease prediction apparatus 200 may predict the cardiovascular disease risk based on the cardiovascular disease risk prediction model generated based on the skin spectrum and pre-generated cardiovascular disease risk classification data.

Here, the cardiovascular disease risk classification data may include user information and risk assessment data based on autofluorescence for the user information. For example, the cardiovascular disease risk classification data may include cardiovascular disease risk that is estimated based on a user's age and skin fluorescence.

For example, the cardiovascular disease risk prediction model may be a prediction model generated by using the skin spectrum, obtained from a subject, as an independent variable, by using, as a dependent variable, the cardiovascular disease risk estimated based on the autofluorescence and age of the subject, and by using Support vector machine (SVM) and Linear discriminant analysis. However, the cardiovascular disease risk prediction model is not limited thereto, and may use various regression analysis algorithms and machine learning for analyzing a correlation between the skin spectrum, obtained from the subject, and the cardiovascular disease risk estimated based on the autofluorescence and age of the subject.

Upon obtaining the skin spectrum, the disease prediction apparatus 200 applies the obtained skin spectrum to the cardiovascular disease risk prediction model, and compares the skin spectrum with risk assessment data which is based on autofluorescence, to determine the cardiovascular disease risk of a user by determining whether autofluorescence corresponding to the obtained skin spectrum exceeds an average autofluorescence for a user's age. The disease prediction apparatus 200 may classify levels of the risk.

Further, the disease prediction apparatus 200 may output at least one or more of a disease prediction result and warning information in operation 630.

For example, the disease prediction apparatus 200 may output at least one or more of the disease prediction result and warning information by using at least one of an acoustic method, a visual method, and a tactile method.

Figure 7:
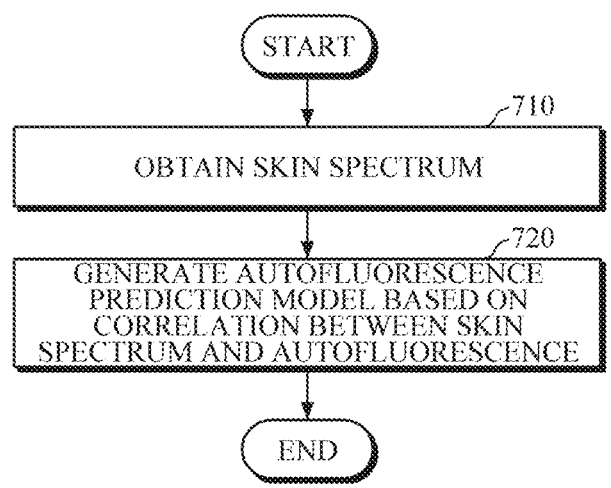
FIG. 7 is a flowchart illustrating a disease prediction model generation method according to an exemplary embodiment.

FIG. 7 is a flowchart illustrating a disease prediction model generation method according to an exemplary embodiment. The disease prediction model generation method may be performed by the disease prediction model generation apparatus 400 of FIG. 4.

Referring to FIGS. 4 and 7, the disease prediction model generation apparatus 400 may obtain a skin spectrum of a subject in operation 710.

In the exemplary embodiment, the skin spectrum may refer to a skin near-infrared absorption spectrum or an optical absorption spectrum of a subject, which is measured from a light that is emitted to and then returned from a skin of the subject. In this case, the disease prediction model generation apparatus 400 may directly generate skin spectrum data by emitting light onto the skin of the subject and detecting light reflected or scattered therefrom, or may receive skin spectrum data of the subject from an external device by communicating with the external device. For example, the skin spectrum of the subject in operation 710 may be different from the skin spectrum of the subject in operation 610, and the subject in operation 710 may also be different from the subject in operation 610. Specifically, the skin spectrum of the subject in operation 710 may be one hundred sample skin spectrums that correspond to skin spectrum 1 through skin spectrum 100 of person 1 through person 100. Skin spectrums 1-100 may be used to generate an autofluorescence prediction model. In order to predict a risk of developing a cardiovascular disease of person 101, the autofluorescence prediction model may be applied to a skin spectrum 101 of the person 101.

Upon obtaining the skin spectrum, the disease prediction model generation apparatus 400 may generate an autofluorescence prediction model based on a correlation between the skin spectrum and autofluorescence of the subject in operation 720.

For example, the disease prediction model generation apparatus 400 may obtain autofluorescence by radiating a UV-A light having a wavelength of 320 nm to 380 nm to the skin of the subject, and may generate the autofluorescence prediction model based on absorbance of the skin spectrum, obtained from the subject, and autofluorescence of the subject.

For example, the disease prediction model generation apparatus 400 may obtain the skin spectrum from the subject and may generate the autofluorescence prediction model by using, as an independent variable, a result of preprocessing of the obtained skin spectrum performed by using at least one preprocessing filter among Multiplicative Scattering Correction (MSC), Standard Normal Variate (SNV) analysis, and/or Savitzky-Golay filter, by using, as a dependent variable, autofluorescence obtained by radiating a UV-A light having a wavelength of 320 nm to 380 nm to the skin of the subject and by using a partial least square (PLS) regression algorithm.

In another example, the disease prediction model generation apparatus 400 may generate a cardiovascular disease risk prediction model based on the skin spectrum of the subject and the pre-generated cardiovascular disease risk classification data. For example, the disease prediction model generation apparatus 400 may generate the cardiovascular disease risk prediction model based on the cardiovascular disease risk classification data, which includes user information and autofluorescence of the subject corresponding to the user information, and the skin spectrum of the subject.

For example, the disease prediction model generation apparatus 400 may generate the cardiovascular disease risk prediction model by using the skin spectrum, obtained from the subject, as an independent variable, by using, as a dependent variable, the cardiovascular disease risk estimated based on the autofluorescence and age of the subject, and by using Support vector machine (SVM) and Linear discriminant analysis. However, the disease prediction model generation apparatus 400 is not limited thereto, and may use various regression analysis algorithms and machine learning for analyzing a correlation between the skin spectrum obtained from the subject and the cardiovascular disease risk estimated based on the autofluorescence and age of the subject.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A disease prediction apparatus, comprising:
a spectrometer configured to obtain an optical spectrum of a subject; and
a processor configured to:
apply the optical spectrum to an autofluorescence prediction model that is generated to predict autofluorescence of the subject and is generated based on a correlation between a reference light absorbance at a wavelength of a light and a reference autofluorescence intensity, wherein the reference light absorbance and the reference autofluorescence intensity are pre-measured from the subject;
predict the autofluorescence of the subject by outputting a result of applying the optical spectrum to the autofluorescence prediction model; and
predict a risk of developing cardiovascular disease based on the predicted autofluorescence.

2. The disease prediction apparatus of claim 1, wherein the processor is further configured to predict the risk of developing the cardiovascular disease based on the predicted autofluorescence and user information of the subject.

3. The disease prediction apparatus of claim 2, wherein the user information comprises at least one of age, gender, race, occupation, stature, body mass index (BMI), smoking status, hemoglobin A1c (HbA1c) concentration of the subject.

4. The disease prediction apparatus of claim 2, wherein the processor is further configured to predict the risk of developing the cardiovascular disease by determining whether the predicted autofluorescence exceeds a predetermined threshold, or whether the predicted autofluorescence exceeds a predetermined autofluorescence for a user's age.

5. The disease prediction apparatus of claim 4, wherein the predetermined autofluorescence for a user's age comprises an average autofluorescence for the user's age.

6. The disease prediction apparatus of claim 2, wherein the processor is further configured to classify levels of the risk of developing the cardiovascular disease according to an extent in which the predicted autofluorescence exceeds a predetermined autofluorescence for a user's age.

7. The disease prediction apparatus of claim 1, wherein the processor is further configured to select the autofluorescence prediction model from among a plurality of auto fluorescence prediction models generated for each group classified based on predetermined information.

8. The disease prediction apparatus of claim 1, wherein the processor is further configured to perform preprocessing on the optical spectrum by using at least one preprocessing algorithm among Multiplicative Scattering Correction (MSC), Savitzky-Golay filter, and Standard Normal Variate (SNV) analysis.

9. The disease prediction apparatus of claim 1, further comprising an output interface configured to output at least one of a disease prediction result and warning information by using at least one of an acoustic method, a visual method, and a tactile method.

10. The disease prediction apparatus of claim 1, wherein the autofluorescence prediction model is generated by using a partial least square (PLS) regression algorithm.

11. The disease prediction apparatus of claim 1, wherein the reference autofluorescence intensity are pre-measured by radiating a UV-A light having a wavelength of 320 nm to 380 nm to the subject.

12. The disease prediction apparatus of claim 1, wherein the optical spectrum of the subject comprises at least one of a near-infrared absorption spectrum, a near-infrared transmission spectrum and a near-infrared reflectance spectrum.

13. A disease prediction method, comprising:
obtaining an optical spectrum of a subject;
applying the optical spectrum to an autofluorescence prediction model that is generated to predict autofluorescence of the subject and is generated based on a correlation between a reference light absorbance at a wavelength of a light and a reference autofluorescence intensity, wherein the reference light absorbance and the reference autofluorescence intensity are pre-measured from the subject;
predicting the autofluorescence of the subject by outputting a result of applying the optical spectrum to the autofluorescence prediction model; and
predicting a risk of developing cardiovascular disease of the subject based on the predicted autofluorescence.

14. The disease prediction method of claim 13, wherein the predicting the risk of developing the cardiovascular disease of the subject comprises predicting the risk of developing the cardiovascular disease based on the predicted autofluorescence and user information of the subject.

15. The disease prediction method of claim 14, wherein the predicting the risk of developing the cardiovascular disease of the subject comprises predicting the risk of developing the cardiovascular disease by determining whether the predicted autofluorescence exceeds a predetermined threshold, or whether the predicted autofluorescence exceeds a predetermined autofluorescence for a user's age.

16. The disease prediction method of claim 15, wherein the predetermined autofluorescence for a user's age comprises an average autofluorescence for a user's age.

17. The disease prediction method of claim 14, wherein the predicting the risk of developing the cardiovascular disease of the subject comprises classifying levels of the risk of developing the cardiovascular disease according to an extent in which the predicted autofluorescence exceeds a predetermined autofluorescence for the user's age.

18. The disease prediction method of claim 13, further comprising:
performing preprocessing on the optical spectrum by using at least one preprocessing algorithm among Multiplicative Scattering Correction (MSC), Savitzky-Golay filter, and Standard Normal Variate (SNV) analysis.

19. The disease prediction method of claim 13, wherein the applying the optical spectrum to the autofluorescence prediction model comprises selecting the autofluorescence prediction model from among a plurality of auto fluorescence prediction models generated for each group classified based on predetermined information.

20. The disease prediction method of claim 13, further comprising: outputting at least one of a disease prediction result and warning information by using at least one of an acoustic method, a visual method, and a tactile method.

* * * * *